United States Patent [19]
Piloian

[11] Patent Number: 5,142,702
[45] Date of Patent: Sep. 1, 1992

[54] UPPER BODY OSTOMY GARMENT

[76] Inventor: Gladys G. Piloian, 585 W. Church Ave., Longwood, Fla. 32750

[21] Appl. No.: 691,570

[22] Filed: Apr. 25, 1991

[51] Int. Cl.$^5$ .............................................. A41D 1/04
[52] U.S. Cl. .................................. 2/102; 2/247; 2/114; 2/250; 2/DIG. 7; 604/345
[58] Field of Search ................ 2/102, 247, 108, 114, 2/250, 252, 253, DIG. 7; 604/345, 343, 344; 224/229, 230

[56] References Cited

U.S. PATENT DOCUMENTS

| | | | |
|---|---|---|---|
| 3,137,862 | 6/1964 | Mizerak | 2/400 |
| 4,262,832 | 4/1981 | Perkins | 2/102 |
| 4,533,355 | 8/1985 | Fair | 2/400 |
| 4,698,848 | 10/1987 | Buckley | 2/250 |
| 4,888,006 | 12/1989 | Beaupied | 604/345 |

Primary Examiner—Werner H. Schroeder
Assistant Examiner—Gloria Hale
Attorney, Agent, or Firm—Richard C. Litman

[57] ABSTRACT

Disclosed is a garment which houses an ostomy appliance. The garment has a rear section, a left section and a right section, of which the sections are combined together such that the left and right sections are secured to the back section. The garment further has an interior pocket for holding the ostomy appliance. The pocket, which is lined with a moisture resistant pliable material for retaining moisture within said pocket, is stitched to the interior of the garment. The pocket further includes a flap for securing the ostomy appliance in place.

9 Claims, 3 Drawing Sheets

UPPER BODY OSTOMY GARMENT

BACKGROUND

1. Field of Invention

The present invention relates to ostomy garments, specifically upper body undergarments for use with ostomy appliances.

2. Description of Prior Art

There are a number of surgical procedures that require the temporary and permanent use of an ostomy appliance. These patients will generally have a stoma at some location on their abdomen through which fluid drainage is needed.

In the past individuals who were in need of the use of ostomy appliances have had to rely upon an encircling belt or other type of undergarment that is worn from the waist down. These types of garments do not address the needs of the user immediately after surgery, and may be an additional cause of irritation in the area surrounding the users stoma.

As a patient begins recovery and their mobility increases, the need for a garment that will allow the patient to move freely about without having to carry the appliance by hand increases. One of the objects of the present invention is to satisfy this need by allowing patient this ability immediately after surgery.

SUMMARY OF THE INVENTION

According to the present invention, a new ostomy garment has been developed which can retain and support one or more ostomy appliances, irrespective of the size of the appliance, the location of the users stoma, or the activities of the user.

The present invention can be worn by the patient at any time after surgery and can be used as soon as the patient is able to walk, allowing the patient mobility without having to carry the ostomy appliance by hand.

The present invention is worn from the shoulders which eliminates the restrictions around the waist area which can cause irritation and discomfort. The present invention provides improved access to the appliances at the same time providing an improved means of retaining and support.

The present invention can be worn under the users normal outer garments and is nonperceptable, this helps improve the users self image aiding in the healing process both physically and emotionally.

DETAILED DESCRIPTION OF DRAWINGS

Figure 1:
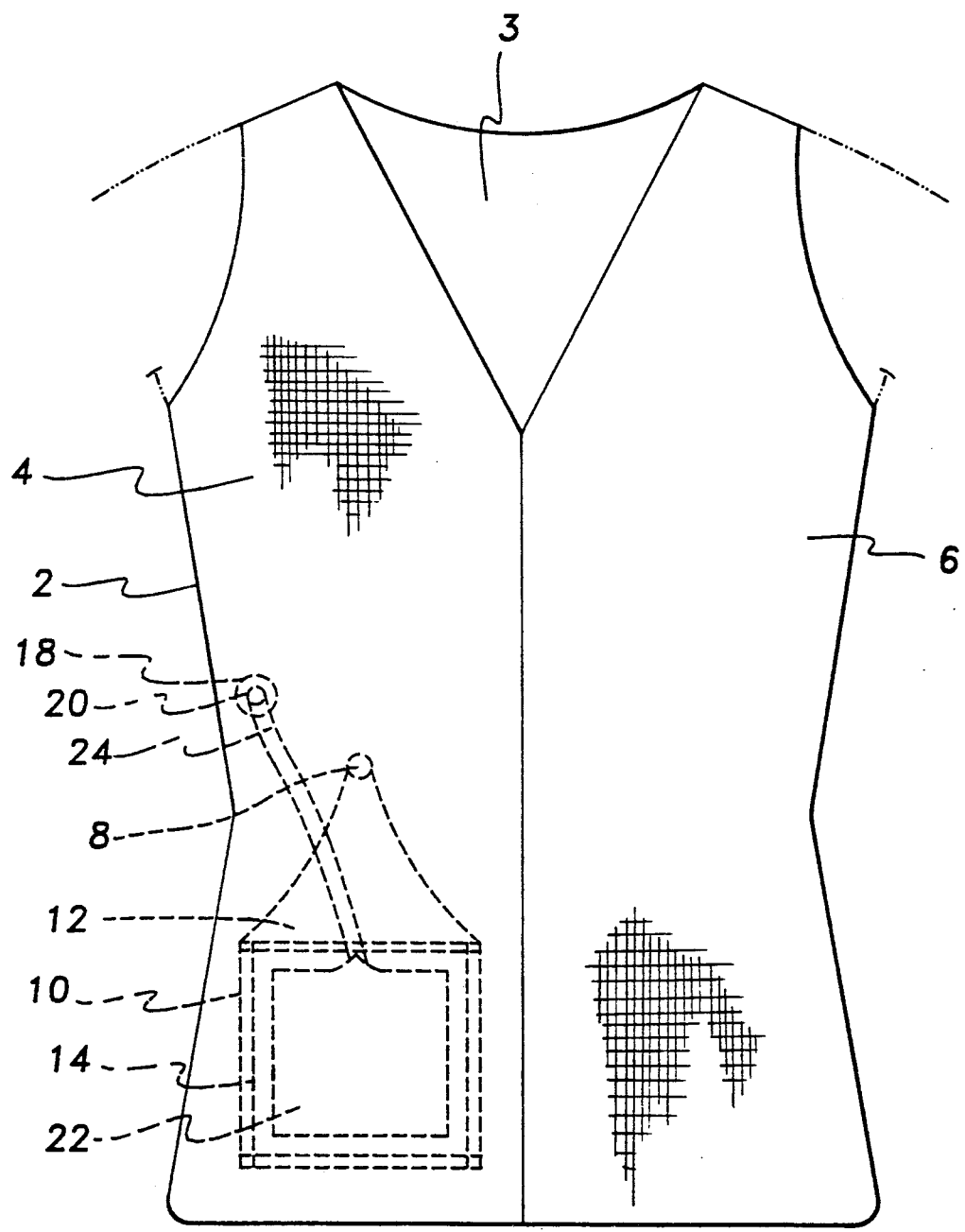
FIG. 1 is a perspective view of the ostomy garment of the preferred embodiment of the invention as worn by the user of an ostomy appliance.

While the embodiment of this invention can be shown in many forms, there is shown in the drawings and will herein be described in detail a preferred embodiment of the invention with the understanding that the present disclosure is to be considered as an exemplification of the invention and is not intended to limit the broad aspect of the invention to the embodiment illustrated.

FIG. 1 shows a perspective view of the ostomy garment 2, as worn by the user of an ostomy appliance 18,20,22,24, and is constructed in accordance with the current invention generally referred to by 2.

An ostomy appliance generally consists of a stoma 20, protruding from the abdomen of the user, surrounded by an adhesive barrier 18, with a tube 24, attached to users stoma 20, and an ostomy pouch 22.

Generally the ostomy garment 2, has a right bodice 4, and a left bodice 6, a rear panel 3, stitched at the shoulders and sides to form the body of the ostomy garment 2.

Figure 2:
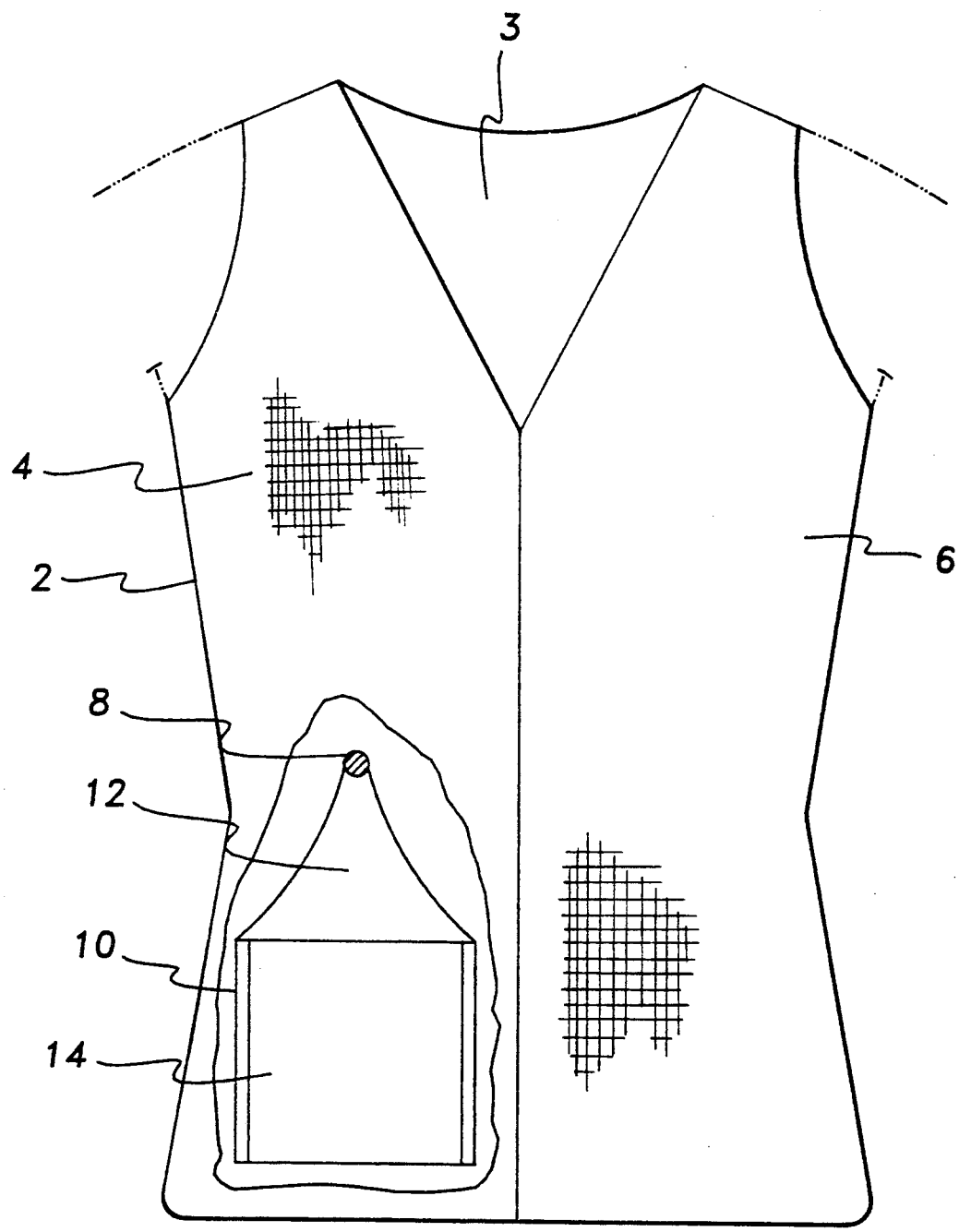
FIG. 2 is a front elevation of the ostomy garment shown in FIG. 1, partly broken away, omitting the ostomy appliance.

FIG. 2 shows a front elevation of the ostomy garment 2, partly broken away on the right bodice 4, FIG. 2 shows the interior retaining pocket 10, having a moisture resistant lining 14, and a flap 12, for securing ostomy pouch 22 in place. Also shown in FIG. 2 is the closure device 8, which is located on pocket flap 12. Closure device can be made of different materials e.g., buttons, snaps, velcro, etc.

Figure 3:
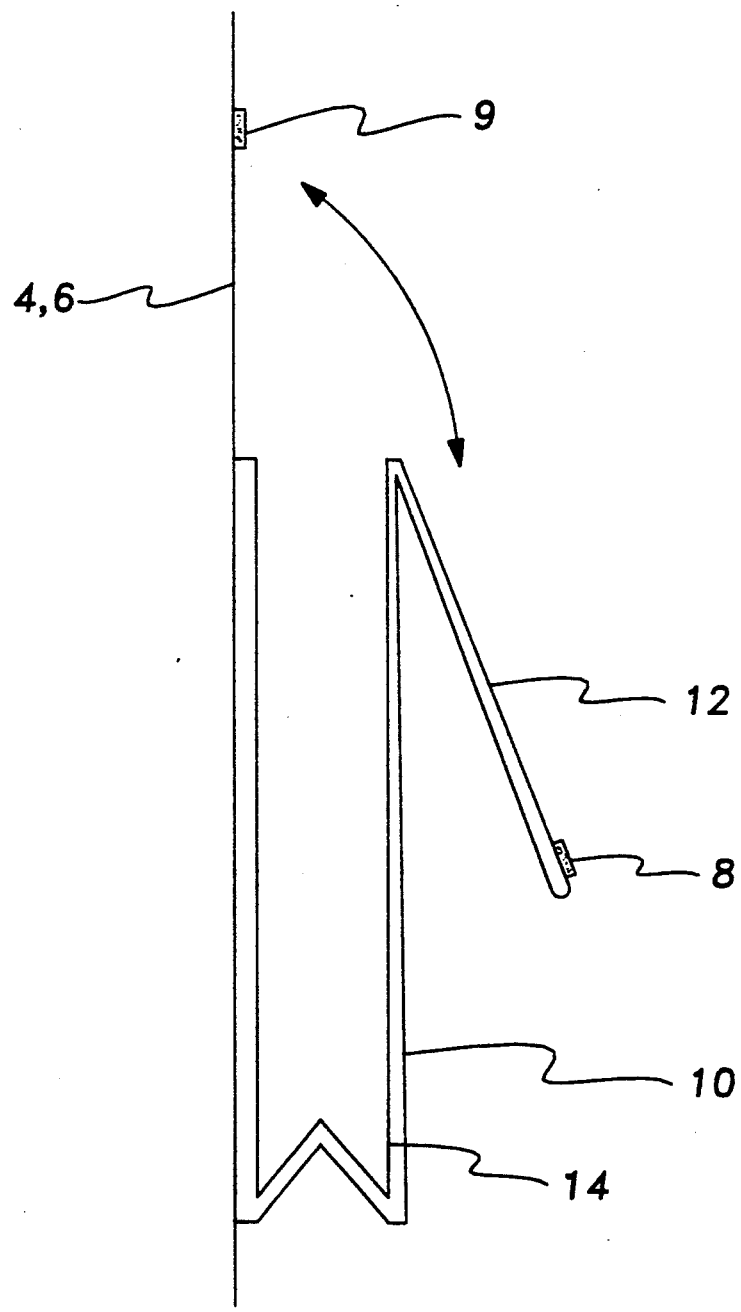
FIG. 3 is a cross-sectional view of the pocket of the ostomy garment of the preferred embodiment of the invention shown in FIG. 1.

FIG. 3 shows a cross-section view of retaining pocket 10, shown with flap 12, in an open position. FIG. 3 shows retaining pocket 10, having a moisture resistant liner 14, stitched inside retaining pocket 10. As can be seen FIG. 3 shows pocket is stitched to interior of right or left bodice 4, 6. Also shown are closure device 8, 9, which are used for securing pocket flap 12 in closed position.

OPERATION OF INVENTION

As shown in FIG. 1, the user of an ostomy appliance 18, 20, 22, 24, will have an adhesive barrier 18, surrounding the stoma 20, through which body fluids are able to leave the body of the user and travel through a flexible tube 24, to the ostomy pouch 22. This pouch is then placed in the interior retaining pocket 10, with the moisture resistant lining 14. Flap 12, of retaining pocket 10, is then closed and secured at the top by the closure device 8, 9. The ostomy garment 10, can then be closed down the front by a number of means e.g., buttons, snaps, velcro, etc. Outer apparel can then be worn over the ostomy garment 10.

While specific embodiments are shown in the drawings, these should not be construed as limiting the scope of the invention, they are merely providing illustrations of some of the presently preferred embodiments of this invention.

Thus the scope of the invention should be determined by the appended claims and their legal equivalents, rather than by the examples given.

What I claim is:

1. A garment for supporting an ostomy appliance comprising:
    an upper body undergarment, which is worn over the shoulders and around the upper portion of a users body, said undergarment includes an interior pocket for holding an ostomy appliance;
    said interior pocket is lined with a moisture resistant pliable material for retaining moisture within said pocket.

2. A garment as claimed in claim 1 wherein said garment has a rear section, a left section and a right section, said sections are combined together such that the left and right sections are secured to the back section.

3. A garment as claimed in claim 1 wherein said garment has an openable front which can be closed by fastening means.

4. A garment as claimed in claim 3 wherein said interior pocket includes a flap, said flap may be closed to secure said ostomy appliance.

5. A garment as claimed in claim 1 wherein said interior pocket includes means for closing said pocket such that said ostomy appliance is held in place.

6. A garment as claimed in claim 3 wherein said garment has a rear section, a left section and a right section, said sections are combined together such that the left and right sections are secured to the back section.

7. A garment as claimed in claim 4 wherein said garment has a rear section, a left section and a right section, said sections are combined together such that the left and right sections are secured to the back section.

8. A garment as claimed in claim 5 wherein said garment has a rear section, a left section and a right section, said sections are combined together such that the left and right sections are secured to the back section.

9. A garment as claimed in claim 1 wherein said interior pocket includes a flap, said flap may be closed to secure said ostomy appliance.

* * * * *